United States Patent
Ali et al.

(10) Patent No.: US 9,682,367 B2
(45) Date of Patent: Jun. 20, 2017

(54) MONOLITH STRUCTURE LOADED WITH METAL PROMOTED NANOZEOLITES FOR ENHANCED PROPYLENE SELECTIVITY IN METHANOL CONVERSION

(71) Applicant: King Fahd University of Petroleum and Minerals, Dhahran (SA)

(72) Inventors: Mohammad Ashraf Ali, Dhahran (SA); Shakeel Ahmed, Dhahran (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 183 days.

(21) Appl. No.: 14/520,978

(22) Filed: Oct. 22, 2014

(65) Prior Publication Data

US 2016/0114314 A1   Apr. 28, 2016

(51) Int. Cl.
| | |
|---|---|
| *B01J 35/04* | (2006.01) |
| *B01J 35/00* | (2006.01) |
| *B01J 37/02* | (2006.01) |
| *B01J 37/08* | (2006.01) |
| *B01J 29/06* | (2006.01) |
| *B01J 29/70* | (2006.01) |
| *B01J 29/76* | (2006.01) |
| *B01J 29/78* | (2006.01) |
| *C07C 1/20* | (2006.01) |

(52) U.S. Cl.
CPC ............... *B01J 29/78* (2013.01); *B01J 29/76* (2013.01); *B01J 35/0006* (2013.01); *B01J 35/04* (2013.01); *B01J 37/0215* (2013.01); *B01J 37/08* (2013.01); *C07C 1/20* (2013.01); *C07C 2529/46* (2013.01); *C07C 2529/48* (2013.01); *C07C 2529/76* (2013.01); *C07C 2529/78* (2013.01); *Y02P 20/52* (2015.11); *Y02P 30/42* (2015.11)

(58) Field of Classification Search
None
See application file for complete search history.

(56) References Cited

U.S. PATENT DOCUMENTS

| | | | | |
|---|---|---|---|---|
| 4,311,865 A | * | 1/1982 | Chen | B01J 29/46 585/408 |
| 2006/0189476 A1 | * | 8/2006 | Deckman | B01D 67/0046 502/60 |

FOREIGN PATENT DOCUMENTS

| | | |
|---|---|---|
| CN | 102531823 A | 7/2012 |
| WO | WO 2014/001412 A2 | 1/2014 |

OTHER PUBLICATIONS

BaiBing Yang, "Preparation of Modified ZSM-5/Cordierite Monolithic Catalyst and Their Catalytic Performance of Methanol to Olefin" 2011 (2 pages).

* cited by examiner

*Primary Examiner* — Colin W Slifka
(74) *Attorney, Agent, or Firm* — Oblon, McClelland, Maier & Neustadt, L.L.P.

(57) ABSTRACT

A catalyst system and a process for methanol to light olefin conversion with enhanced selectivity towards propylene. The catalyst system comprises a honeycomb monolith catalyst support coated with nanozeolite catalysts on the edges and inside the channels of the support structure. The nanozeolite catalysts have been pre-modified with metal. The catalyst system gives higher hydrothermal stability to the catalyst compared to randomly packed pellet catalyst and allows methanol to be converted to predominantly propylene at a low temperature, with decreased selectivity towards $C_2$, higher olefins and paraffinic hydrocarbons.

20 Claims, 1 Drawing Sheet

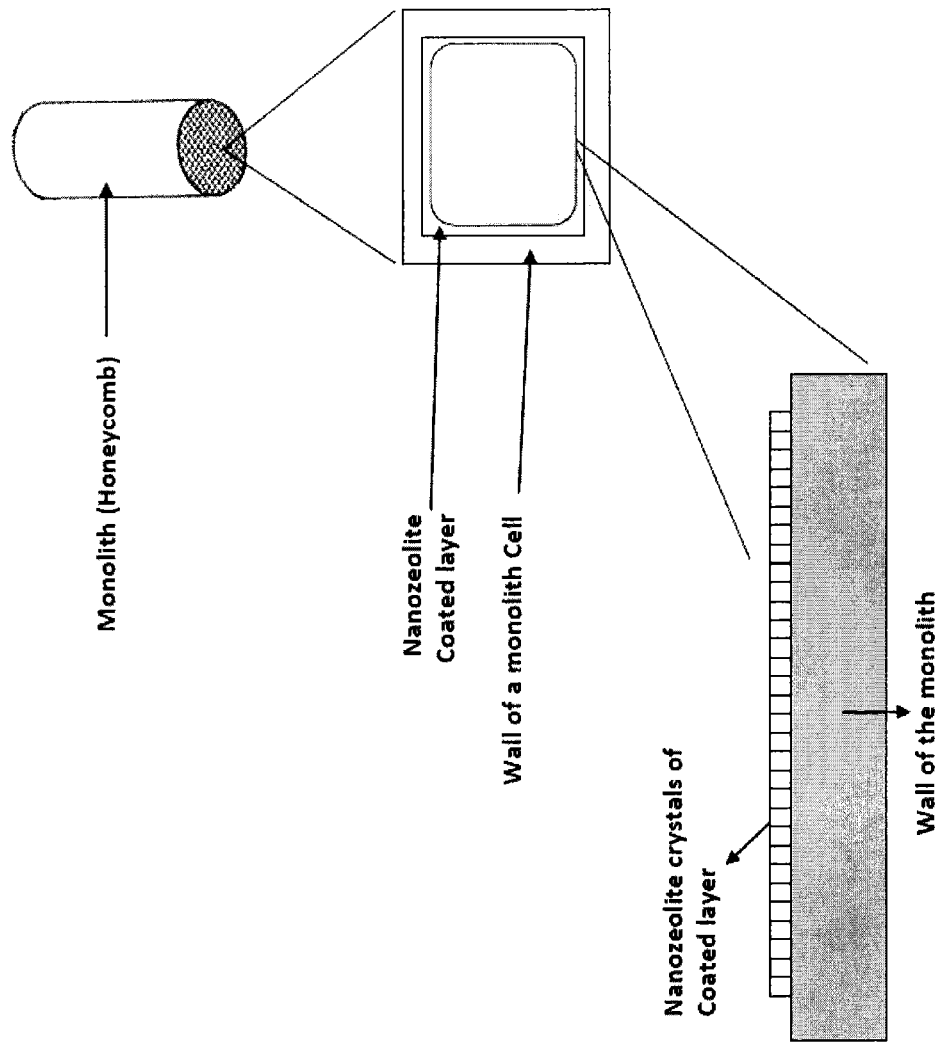

MONOLITH STRUCTURE LOADED WITH METAL PROMOTED NANOZEOLITES FOR ENHANCED PROPYLENE SELECTIVITY IN METHANOL CONVERSION

BACKGROUND OF THE INVENTION

Technical Field

The present invention relates to a process and a catalyst for converting methanol into light olefins. More specifically, the process and the catalyst increase the selectivity of the methanol conversion to propylene.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Increasing cost and uncertain supply of crude oil has prompted the search for alternative processes for producing hydrocarbon products. One such process is the conversion of methanol into light olefins such as ethylene, propylene and butylenes. There is a specific interest in the use of methanol to produce light olefins due to the fact that methanol is being produced worldwide in large quantity from natural gas through the production of synthesis gas (mixture of CO and $H_2$) from methane gas which is then converted to methanol. Methanol can also be produced from coal and biomass processing. Methanol is converted commercially into propylene using randomly packed pellet catalysts. This process has limitations, such as lower selectivity to propylene and higher yields of byproducts such as $C_2$, $C_4$ and $C_5+$ olefins and paraffinic hydrocarbons.

Processes for converting methanol to light olefins are well known in the prior art. Early catalysts used for this conversion reaction were based on aluminosilicates molecular sieves. These processes have been described in U.S. Pat. Nos. 4,238,631, 4,328,384, 4,423,274 and 4,499,327 (each incorporated herein by reference in its entirety). These patents reveal the deposition of coke onto the molecular sieves in order to increase selectivity to light olefins and minimize the formation of $C_5$ and higher hydrocarbons ($C_5+$) hydrocarbons as byproducts. The effect of the coke is to reduce the effective pore diameter of the molecular sieves. The prior art also disclose that silicoaluminophosphates molecular sieves can be used to catalyze the methanol to olefin process.

Propylene is perhaps one of the oldest and most important of the crucial building blocks of the petrochemical industry and one of the principal light olefins. From propylene, important industrial derivatives such as polypropylene, acrylonitrile, propylene oxide, 2-propanol, cumene/phenol, oxo-alcohols, isopropanol, acrylic acids, and oligomers are obtained. Various additional products use propylene as a feedstock. Hence, its use can be seen to span a wide span of end-use industries, from automotive and construction, to polymers, consumer durables, packaging, medical, and electronics.

Historically, propylene was readily available, either as a co-product of heavy liquids cracking or from refinery sources. Growth in demand for propylene derivatives has outpaced that for ethylene derivatives for several years. The higher propylene demand has largely absorbed readily available sources of propylene to yield, until now, a fairly balanced global market in terms of propylene supply and demand. However, an interesting dynamic is now unfolding in the United States whereby large amounts of natural gas from shale and other sources are being produced with their accompanying natural gas liquids (NGLs) such as ethane, propane and butanes. This additional NGL is being utilized in higher percentages in steam crackers, which in turn, is lowering available propylene supplies and changing the competitiveness of the North American ethylene chain.

With the recent discovery of U.S. shale gas reserves and the increase in ethane cracking currently taking place that is set to only increase exponentially in coming years, U.S. propylene supply tightened by large amounts. This is because the cracking of light feedstocks produces dramatically less propylene co-product than the cracking of heavy liquids. Consequently, propylene production in the United States from ethylene crackers has declined, and, for the first time in 20 years, propylene prices were higher than ethylene prices. This propylene supply/demand gap is projected to considerably widen in the next few years as propylene demand rises and even greater volumes of lighter feedstocks available from shale gas deposits rapidly replace heavy liquids in crackers. LPG cracking in Europe will have a similar impact, although the displacement of hydrocarbon liquids will not be nearly as pronounced as in North America. Hence, shortages of propylene feedstock are likely in these two regions—imbalances which will extend to other regions via higher propylene pricing.

In view of the foregoing, there exists a considerable need for new processes and catalysts for methanol conversions to light olefins with improved selectivity towards propylene and also preferably a lower coking of the catalyst.

BRIEF SUMMARY OF THE INVENTION

In a first aspect, the present invention relates to a catalyst system for the conversion of methanol into light olefins comprising zeolite nanoparticles modified with at least one promoter metal and a honeycomb monolith support coated with the zeolite nanoparticles on the edges and inside the channels of the honeycomb monolith support. The zeolite nanoparticles are selected from the group consisting of metal modified nanoaluminosilicates, nanosilicates and a combination thereof. Preferably, the zeolite nanoparticles are microporous molecular sieves having an MFI framework type. The promoter metal is at least one selected from the group consisting of iron, cobalt, nickel and chromium.

In one embodiment, the catalyst system further comprises a binder.

In one embodiment, the zeolite nanoparticles of the catalyst system further comprise alkaline earth metal ions.

In certain embodiments, the methanol conversion catalyzed is shows selectivity towards propylene of at least 40-80% of the total mass of products.

In a second aspect, the present invention relates to a process of converting methanol into light olefins, comprising contacting the methanol in a reactor with a catalyst system comprising zeolite nanoparticles modified with at least one promoter metal and a honeycomb monolith support coated with the zeolite nanoparticles on the edges and inside the channels of the honeycomb monolith support.

Preferably, the methanol is in vapor phase.

Preferably, the process is carried out at a pressure of 0 psig to 50 psig.

Preferably, the process is carried out in the presence of an inert gas.

The process may be conducted in a fixed-bed reactor or a moving-bed reactor.

In a third aspect, the present invention relates to a method of preparing a catalyst system, comprising modifying zeolite nanoparticles with at least one promoter metal selected from the group consisting of iron, cobalt, nickel and chromium, optionally mixing the metal-modified zeolite nanoparticles with a binder, coating a honeycomb monolith with the metal-modified zeolite nanoparticles, and optionally a binder, on the edges and inside the channels of the honeycomb monolith and calcinating the coated honeycomb monolith.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIG. 1 a schematic diagram illustrating the monolith honeycomb structure with modified nanozeolite coating.

DETAILED DESCRIPTION OF THE EMBODIMENTS

Referring now to the drawings, wherein like reference numerals designate identical or corresponding parts throughout the several views.

The present invention pertains to a catalyst system or a catalytic composite comprising a honeycomb monolith catalyst support or carrier loaded with metal modified nanozeolite catalysts (see FIG. 1) for methanol conversion into light olefins at low pressure, with high selectivity towards propylene and low selectivity towards $C_2$, $C_4$, $C_5+$ olefins, paraffins and other hydrocarbon byproducts. In other words, the catalyst system or catalytic composite of the present invention is effective in converting methanol into predominantly propylene, i.e. at least 40% of the total mass of products, preferably 50-70%, even more preferably 60-80%.

For purposes of the present invention, "catalyst system" and "catalytic composite" refer to materials such as an initiator or a catalyst, an activator or a promoter that enhances the activity of the catalyst, a catalyst support or a carrier for the mounting or loading of the catalyst and the promoter, a binder that enhances the loading of the catalyst and the promoter onto the catalyst support. These materials, in combination, cause chemical reactions to begin. Promoters may be part of the catalysts, for example, being adsorbed to the surface of catalyst particles. The catalyst support is usually inert towards the catalyzed reaction. In a preferred embodiment, the catalyst, promoter, binder are loaded only on the exterior surface of the catalyst support.

For purposes of the present invention, "light olefins" refers to ethylene, propylene and butylene.

The monolithic-nanozeolite catalyst system according to the present invention may be used in methanol-based propylene production facilities as well as in existing methanol to propylene conversion units.

Other petrochemical catalytic reactions that are conducted on randomly packed pellet catalyst systems may also benefit from the monolithic catalyst support structure loaded with metal-modified or metal-promoted nanozeolite crystals. This is especially true for petrochemical reactions wherein selectivity towards certain products is desired and large gas volumes are to be treated. The honeycomb monolith structure comprising a large number of parallel channels provides high contact efficiencies between the monolith and gas flow streams, offers a very low pressure drop, short diffusion lengths and no obstruction by particulate matter. The diffusion limitation of monolithic-nanozeolite catalyst systems can be significantly reduced as compared to randomly packed pellet catalysts.

The metal for modification or promotion of nanozeolites, of the catalyst promoter, is a rare earth metal selected from, but not limited to, the group consisting of iron, cobalt, nickel, chromium and combinations thereof. In one embodiment, the metal particles are nanoparticles, with an average particle diameter of 1-10 nm, preferably no greater than 5 nm, and preferably having an average particle diameter of 2-4 nm. The amount of promoter metal in the catalyst may be 5-15 wt. % of the total weight of the catalyst system, with the remaining weight attributed to the monolithic catalyst support and nanozeolites. In another embodiment, the amount of nanozeolites may be preferably 7-12 wt. % of the catalyst system, even more preferably 8-10 wt. %.

Similarly, the nanozeolite crystals have an average particle diameter of 10-700 nm, preferably no greater than 100 nm, and preferably having an average particle diameter of 50-85 nm, more preferably 10-70 nm, even more preferably 10-50 nm. The particle size distribution of the metallo-nanozeolites is such that more than 95%, preferably more than 98% or more than 99% of the particles have a particle size of less than 50 nm. The size of zeolite crystals is crucial as large crystals tend to further crack the propylene formed, thus causing the reaction to lose propylene selectivity.

The nanozeolite crystals may be modified by wetness impregnation method using a solution containing one of the aforementioned metals. The impregnation process may involve a plurality of precursor and intermediate compounds.

The nanozeolite catalysts are metalloaluminosilicate, metallosilicalite or combinations thereof. In one embodiment, the amount of metallonanozeolites in the catalytic system may be 5-50 wt. % of the total weight of the catalyst system, with the remaining weight attributed to the monolithic catalyst support. In another embodiment, the amount of metallonanozeolites may be 5-35 wt. % of the catalyst system, preferably 5-25 wt. %. When both metalloaluminosilicate and metallosilicalite are present as catalysts, the amounts of the two components may be adjusted according to metalloaluminosilicate to metallosilicalite mass ratios of 1:1, 1:2, 1:3, 1:4, 4:1, 3:1 and 2:1.

Preferably, the nanozeolite catalysts are molecular sieves on the edges and inside the channels of the honeycomb monolith support, with three-dimensional microporous MFI framework structure of $Al_2O_3$ and $SiO_2$ tetrahedral units, for example, ZSM-5 in its H-form. As used herein, the molecular sieves have pore diameters of less than 2 nm. The zeolites are unique group of molecular sieves that are structured as a lattice of silica and optionally alumina, and are protonic with exchangeable cations such as alkali or alkaline earth metal ions. Examples of these alkaline earth metal ions include magnesium (Mg), beryllium (Be), calcium (Ca), strontium (Sr), barium (Ba) and radium (Ra). The term zeolite also included technically and structurally related materials similar to zeolites but in which the silica and alumina may be replaced totally or partially with other oxides.

It may be advantageous to incorporate catalyst promoter with the catalyst or into the monolith support structure. Promoters function as co-catalysts and increase the overall catalytic activity of the catalyst and product selectivity with little increase in overall catalysis costs. Suitable promoters may be selected from a wide variety of rare earth metals as previously described. One promoter that has been found to be particularly effective is iron, and a particularly effective combination is the use of iron promoter with ZSM-5 zeolite catalyst. This catalyst-promoter combination may be used to impregnate a cordierite monolith support for use in the methanol to propylene reaction according to the present invention. The catalyst-promoter combination may be co-extruded with the monolith support material.

The effects of metal modification of the nanozeolite crystals may be evaluated by characterizing and comparing the physical and chemical properties of the non-modified and modified crystals. Physical properties such as morphology, surface area, dispersion and composition may be characterized using different techniques, for example, scanning electron microscopy (SEM), thermo-gravimetric analysis (TGA), X-ray diffraction (XRD) and energy dispersive X-ray spectroscopy), differential scanning calorimetry (DSC), Brunauer-Emmett-Teller (BET) adsorption and Fourier transform infrared (FTIR).

The BET surface area of the obtained nanozeolite crystals impregnated with iron, cobalt, nickel or chromium is 100-1000 $m^2g^{-1}$, preferably 200-800 $m^2g^{-1}$, or 300-600 $m^2g^{-1}$. The unmodified nanozeolite crystals have a BET surface area of 100-300 $m^2g^{-1}$.

The pore size distribution of the metal-impregnated nanozeolites is 0.6-1.0 nm, preferably 0.7-0.8 nm.

The monolith structure loaded on edges and inside channels, with metalloaluminosilicate/metallosilicate MFI type catalyst, of this invention may be mixed with a binder to provide better loading on the monolith structure. Examples of the binders that can be used include alumina, silica, aluminum-phosphate, silica-alumina, and their mixtures. Preferably, the binder is present only on the exterior surface of the metal modified nanozeolite crystals and the honeycomb monolith support. Preferably the zeolite nanoparticles and/or the metal catalyst is present only on the surfaces of the monolith structure and not incorporated within the support material used to make the monolith structure.

The conversion of methanol to light olefins is effected by contacting the methanol with the monolith structure loaded with metalloaluminosilicate molecular sieve catalyst at conversion conditions, thus forming the desired light olefins. The methanol may be in the liquid or vapor phase. Preferably, the methanol is in vapor phase. Contacting the methanol with honeycomb monolith support loaded with metal modified nanozeolites can be done in a continuous mode or a batch mode with a continuous mode being preferred. The amount of time that the methanol is in contact with the metalloaluminosilicate molecular sieve catalyst must be sufficient to convert the methanol to the desired light olefin products. The longer contact times are used at lower temperatures while shorter times are used for reaction at higher temperatures. Furthermore, when the process is carried out in a continuous mode, the weight hourly space velocity (WHSV) based on methanol can vary from about 1 $hour^{-1}$ to about 1000 $hour^{-1}$ and preferably from about 10 $hour^{-1}$ to about 100 $hour^{-1}$.

Generally, the process is carried out at elevated temperatures in order to form light olefins at a sufficiently high rate. Thus, the process should be carried out at a temperature of about 300° C. to about 600° C., preferably from about 400° C. to about 550° C. The monolithic-nanozeolite catalyst system according to the present invention records a hydrothermal stability of 25° C. to 650° C. The process may be carried out over a wide range of pressure including autogenous pressure. Thus, the pressure can vary from about 0 psig to about 250 psig, preferably from about 5 psig to about 50 psig. Preferably, the methanol to propylene conversion process is carried out in the presence of nitrogen, argon, helium, carbon dioxide and mixtures thereof, as well as an oxygen content of less than 0.01%, preferably none.

The methanol feedstock may be diluted with inert diluents in order to efficiently convert methanol into olefins. Examples of the diluents which may be used are helium, argon, nitrogen, carbon monoxide, carbon dioxide, and hydrogen and their mixtures. The amount of diluents used can vary considerably and is usually from about 5 to about 50 mole percent of the feedstock and preferably from about 25 to about 50 mole percent.

The actual configuration of the reaction zone may be any well-known catalyst reaction zone known in the art. Thus, a single reaction zone or a number of zones arranged in series or parallel may be used. In such reaction zones the methanol feedstock is flowed through a bed containing the monolith structure loaded with nanozeolite catalysts. When multiple reaction zones are used, one or more monolith structures loaded with catalyst may be used in series to produce the desired product mixture. If regeneration is required, the monolith structure loaded with catalyst can be continuously introduced as a moving bed to a regeneration zone where it can be regenerated by oxidation in an oxygen containing atmosphere to remove carbonaceous materials. Therefore, the catalyst system disclosed herein may be used in a fixed-bed reactor or a moving-bed reactor.

In one embodiment, the honeycomb monolith support structure loaded with metal modified nanozeolite crystals may be placed within or on top of a packed bed of a reactor in a vertical orientation.

In one embodiment, the packed bed consists of only the loaded honeycomb monolith structure.

As shown in FIG. 1, honeycomb monoliths are continuous, unitary ceramic or metallic structures, with long parallel and straight channels extended through the body, which are separated by thin walls. The first monolithic structures had hexagonal-shaped passages that gave a honeycomb appearance to the cross section of the monolith. Monolithic structures that can be used in the present invention can be of different channel shapes, for example, square which is probably the most popular due its simplicity.

Monoliths according to the present invention, for example, can be used with a honeycomb shape with 62-186 channels per square centimeter (400-1200 cpsi=cells per square inch), wherein monoliths are preferred with a honeycomb shape with 78-171 channels per square centimeter (500-1100 cpsi), more preferably those with 93-163 (600-1050 cpsi), more preferably those having 109-155 (700-1000 cpsi), more preferably those with 124-147 (800-950 cpsi), more preferably those with 132-144 (850-930 cpsi). In an alternative embodiment, honeycombs with 8-124 channels per square centimeter (50 to 800 cpsi), preferably (150 to 700 cpsi), more preferably those having from 31 to 93 (200 to 600 cpsi), more preferably 39 to 85 (250 to 550 cpsi) and further preferably those 47 to 78 (300 to 500 cpsi), may be used. In yet another alternative embodiment, more monoliths of honeycomb shape with 54-70 channels per square centimeter (350 to 450 cpsi) may be used.

Generally catalyst systems comprise porous, inorganic structure in shaped forms such as extrudates and beads or a sintered ceramic, which is the monolith support, which serves as a substrate for active catalyst applied to it through impregnation process. The porous structure may be prepared as honeycomb, a solid matrix containing both channels and pores; foam, a solid cellular structure, non-woven fibrous structures and their combinations. A honeycomb or monolith structure is usually prepared by extrusion process. The monolith support has high pore density and thin walls which facilitate monolith catalyst system to endure the severity of the chemicals reactions for which it is used. The monolith structure may have any particular desirable configurations, but it should not hinder the flow of the reactants.

The monolith catalyst system according to the present invention may be prepared using a suitable material that is capable of resisting the reaction temperatures and pressures and is non-reacting to the selected catalyst and the reactants. Such materials include cordierite (magnesium aluminum silicate); silicon carbide, silicon nitride, silica-thoria, silica-alumina-thoria, alpha alumina, theta alumina, magnesia, metals and alloys, zirconium phosphate, silica-titania, alumina-titania and their combinations. The monolith catalyst material also may also be a composite material into which a catalyst is incorporated during its preparation.

The nanozeolite catalysts in powder form are coated on the edges and walls of the substrate using one or more coating or impregnation processes. The coating could be achieved through impregnation process in which the catalyst is deposited by dipping the substrate in a liquid mixture of zeolite and dried repeatedly. After achieving the required coating, the structure is calcined to create a strong bonding between the catalyst particles and the substrate structure.

During the reaction process, the reactant methanol is passed through the inorganic monolith structure wherein it is in contact with the catalyst deposited on the edges and walls of the structure, with the result that the desired reaction is effectively catalyzed and thus facilitated. Selection of a suitable catalyst may be made from the catalysts that are capable of catalyzing the conversion of methanol into propylene. Such catalysts are desirably further capable of impregnating or being co-formed with a given selected monolith support. Impregnation as used herein refers to the significant absorption and retention, within the pores of the ceramic, of the catalyst, the catalyst therefore being in a liquid, slurry or gaseous form prior to absorption. Such absorption is furthermore preferably such that the catalyst does not occlude the pores in such a way that the reactants are not able to efficiently flow through the monolith pores. In a supplemental or alternative scheme, co-forming refers to incorporation of the catalyst within and throughout the inorganic matrix in conjunction with formation of the structure, by means such as co-extrusion. In either case the adherence of the catalyst to the inorganic monolith support may be facilitated by use of conventional binders, or the catalyst and monolith support materials may be selected to obtain suitable adhesion or cohesion between them.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

The invention claimed is:

1. A catalyst system for the conversion of methanol into light olefins comprising:
   zeolite nanoparticles in the form of crystals having an average particle diameter of 10-50 nm modified with at least one promoter transition metal selected from the group consisting of iron, nickel, and chromium in the form of nanoparticles with an average particle diameter of 1-10 nm adsorbed onto a surface of the zeolite nanoparticles; and
   a honeycomb monolith support with 400-1200 cells per square inch coated with the zeolite nanoparticles on the edges and inside the channels of the honeycomb monolith support;
   wherein the catalyst system comprises 5-15 wt % of the promoter transition metal relative to the total weight of the catalyst system; and
   wherein the catalyst is capable of converting methanol to propylene with a selectivity towards propylene of at least 40% relative to a total mass of light olefin products and a selectivity towards propylene that is greater than a selectivity towards ethylene relative to a total mass of light olefin products and that is greater than a selectivity towards butylene relative to a total mass of light olefin products.

2. The catalyst system of claim 1, wherein the zeolite nanoparticles comprise metalloaluminosilicates and metallosilicalites of at least one transition metal selected from the group consisting of iron, nickel and chromium and wherein a ratio of metalloaluminosilicates to metallosilicalites is in a range from 1:1 to 2:1.

3. The catalyst system of claim 1, wherein the zeolite nanoparticles are microporous molecular sieves having an MFI framework type, which have a BET surface area of 100-1000 $m^2g^{-1}$ and which have a pore size distribution of 0.6-1.0 nm.

4. The catalyst system of claim 1, wherein the promoter transition metal is iron.

5. The catalyst system of claim 1, further comprising a binder.

6. The catalyst system of claim 1, wherein the zeolite nanoparticles further comprise alkaline earth metal ions.

7. The catalyst system of claim 1, wherein the selectivity of the conversion towards propylene is 40-80% of the total mass of light olefin products.

8. A process of converting methanol into light olefins, comprising:
   contacting the methanol in a reactor with the catalyst system of claim 1.

9. The process of claim 8, wherein the methanol is in vapor phase.

10. The process of claim 8, wherein the process is carried out at a pressure of 0 psig to 50 psig.

11. The process of claim 8, wherein the process is carried out in the presence of an inert gas.

12. The process of claim 8, wherein the reactor is selected from the group consisting of a fixed-bed reactor and a moving-bed reactor.

13. The process of claim 8, wherein the zeolite nanoparticles comprise metalloaluminosilicates and metallosilicalites of at least one transition metal selected from the group consisting of iron, nickel and chromium.

14. The process of claim 8, wherein the zeolite nanoparticles are microporous molecular sieves having an WI framework type.

15. The process of claim 8, wherein the promoter transition metal is iron.

16. The process of claim 8, wherein the catalyst system further comprises a binder.

17. The process of claim 8, wherein the zeolite nanoparticles further comprise alkaline earth metal ions.

18. The process of claim 8, wherein the selectivity of the conversion towards propylene is 40-80% of the total mass of light olefin products.

19. A method of preparing the catalyst system of claim 1, comprising:
  (a) modifying zeolite nanoparticles with at least one promoter transition metal selected from the group consisting of iron, nickel and chromium;
  (b) optionally mixing the metal-modified zeolite nanoparticles with a binder;
  (c) coating the honeycomb monolith with the metal-modified zeolite nanoparticles, and optionally a binder, on the edges and inside the channels of the honeycomb monolith; and
  (d) calcining the coated honeycomb monolith;
  wherein the zeolite nanoparticles are microporous molecular sieves having an WI framework type.

20. The method of claim 19, wherein the zeolite nanoparticles comprise metalloaluminosilicates, metallosilicalites of at least one transition metal selected from the group consisting of iron, nickel and chromium.

* * * * *